United States Patent [19]

Bruzzese et al.

[11] Patent Number: 4,562,203
[45] Date of Patent: Dec. 31, 1985

[54] RIFAMYCINS DERIVATIVES AND PREPARATION AND PHARMACEUTICAL COMPOSITIONS THEREOF

[75] Inventors: Tiberio Bruzzese; Ernani Dell'Acqua; Holger H. Van Den Heuvel, all of Milan, Italy

[73] Assignee: SPA Societa Prodotti Antibiotici S.p.A., Italy

[21] Appl. No.: 589,335

[22] Filed: Mar. 14, 1984

[30] Foreign Application Priority Data

Mar. 24, 1983 [IT] Italy .................................. 20278/83

[51] Int. Cl.[4] .................. A61K 31/395; C07D 498/08
[52] U.S. Cl. ............................. 514/468; 260/239.3 P; 514/212; 514/323; 514/408; 514/237; 514/236; 514/183
[58] Field of Search .................. 260/239.3 R; 424/244, 424/248.54, 267, 274

[56] References Cited

U.S. PATENT DOCUMENTS

| | | | |
|---|---|---|---|
| 3,342,810 | 9/1967 | Maggi et al. | 260/239.3 P |
| 4,017,481 | 4/1977 | Marsili et al. | 260/239.3 P |
| 4,086,225 | 4/1978 | Marsili et al. | 260/239.3 P |
| 4,116,957 | 9/1978 | Rossetti et al. | 260/239.3 P |
| 4,124,585 | 11/1978 | Marsili et al. | 260/239.3 P |
| 4,124,586 | 11/1978 | Marsili et al. | 260/239.3 P |
| 4,164,499 | 8/1979 | Rossetti et al. | 260/239.3 P |
| 4,165,317 | 8/1979 | Rossetti et al. | 260/239.3 P |
| 4,175,077 | 11/1979 | Rossetti et al. | 260/239.3 P |
| 4,219,478 | 8/1980 | Marsili et al. | 260/239.3 P |
| 4,226,765 | 10/1980 | Marsili et al. | 260/239.3 P |
| 4,305,941 | 12/1981 | Marsili et al. | 424/248.54 |
| 4,327,096 | 4/1982 | Marsili et al. | 424/250 |
| 4,372,961 | 2/1983 | Bruzzese et al. | 424/267 |
| 4,447,432 | 5/1984 | Franceschi et al. | 260/239.3 P |

*Primary Examiner*—Robert T. Bond
*Attorney, Agent, or Firm*—Ostrolenk, Faber, Gerb & Soffen

[57] ABSTRACT

The invention relates to new rifamycins derivatives endowed with antibiotic activity and process for their preparation.

The new rifamycins derivatives have the formula:

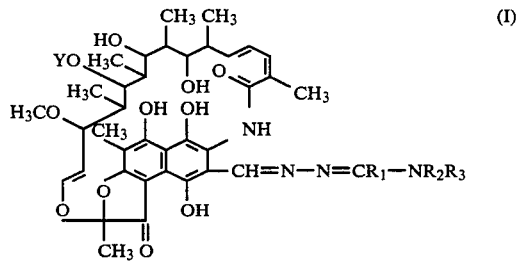

(I)

20 Claims, No Drawings

RIFAMYCINS DERIVATIVES AND PREPARATION AND PHARMACEUTICAL COMPOSITIONS THEREOF

The invention relates to derivatives of rifamycins having antibiotic activity and to processes for making same.

The rifamycin derivatives of the present invention correspond to the following structural formula:

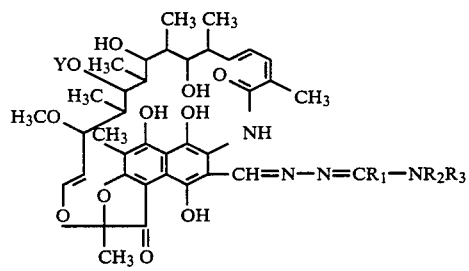

wherein:
Y=H or CH₃—CO;
$R_1$ is an alkyl group with up to 4 carbon atoms;
$R_2$ is an alkyl group with up to 6 carbon atoms, an alkenyl group with up to 5 carbon atoms, a cycloalkyl group having from 5 to 7 carbon atoms, an aryl, benzyl, or substituted benzyl group;
$R_3$ is an alkyl group with up to 6 carbon atoms or an alkenyl group with up to 5 carbon atoms; or
—$NR_2R_3$ is a ring with up to 7 carbon atoms possibly substituted with one or more low molecular weight alkyls and possibly comprising an S or O heteroatom.

The derivatives of formula (I) are derivatives of rifamycin SV and, obviously, the invention also covers the corresponding derivatives of rifamycin S, i.e. the quinone derivatives of the compounds of formula (I).

As it is known in the art, rifamycin SV is a compound related to rifamycins, a group of antibiotics characterized by a natural ansa structure (chromophoric naphthohydroquinone group spanned by a long aliphatic bridge) isolated from a strain of *Streptomyces mediterranei* (v.P.Sensi et al. U.S. Pat. No. 3,313,804).

Rifamycin SV and rifamycins in general, particularly rifampicin, are very active in causing various biological responses as for instance: inhibition of DNA-dependent RNA polymerase and the consequent interference with the synthesis of nucleic acids in micro-organisms. Thus, rifamycins are active against Gram-positive bacteria as well as some mycobacteria, especially *M.tuberculosis* and *M.leprae;* they are also active against some Gram-negative bacteria inclusive of *Neisseria gonorrhoeae* and *N.meningitidis;* at high concentrations, they are also active against some viruses.

Because of these activities, rifamycin SV and rifampicin are useful in preventing, controlling or alleviating a great variety of diseases in humans and animals.

Minimum inhibitory concentrations tend to vary with the medium used but Gram-positive organisms are generally inhibited by 0.002–0.5 μg/ml, whereas Gram-negative micro-organisms by 1–10 μg/ml and mycobacteria by 0.005–2 μg/ml.

Daily dosage regimens are 125–500 mg for rifamycin SV and 150–900 mg for rifampicin: however, both drugs are endowed with a very short half-life (rifampicin: 4–8 hours and) thus require frequent administration. What is more, rifamycin SV is scarcely adsorbed from the gut and has to be administered, for the systematic therapy, only by injection.

It has now been found that the inventive rifamycin derivatives of formula (I), while often maintaining a similar or greater potency against the several microorganisms, have some additional advantages: many of them are almost completely adsorbed by the oral route thus giving very high blood levels; additionally, when tested for screening purposes in mice, they often gave blood levels at 24 hours many times higher than rifampicin administered in comparison at the same dose, thus demonstrating a much more prolonged half-life (to 20 hours or more). Also at 48 and 72 hours, levels of potentially therapeutic value were found.

The toxicity of the inventive compounds of formula (I) is generally quite satisfactory.

The therapeutic dosage regimen for the inventive rifamycin derivatives of formula (I) will depend upon a variety of factors, including the type, age, weight and medical condition of the patient as it is known to those skilled in the art. Doses in the range of 150–600 mg per day are normally administered; the same doses on alternate days are quite sufficient for the longest acting compounds.

The derivaties of formula (I) of the present invention may be obtained by various processes.

According to the first process of the present invention, the hydrazone of the 3-formyl-rifamycin SV is dissolved in a suitable solvent such as, e.g. chloroform, methylene chloride or tetrahydrofuran and reacted with a reactive derivative of an amide or thioamide of formula

wherein $R_1$, $R_2$, $R_3$ and

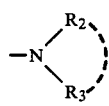

are as above defined and $R_4$=O or S.

The hydrazone of 3-formyl-rifamycin SV may, for example, be prepared directly by reacting 3-formyl-rifamycin SV with hydrazine, following the process described in Example 8 of U.S. Pat. No. 3,342,810, or, indirectly, by reacting hydrazine with reactive derivatives of 3-formyl-rifamycin SV. In this case it is possible to advantageously use, for example, a Schiff's base between 3-formyl-rifamycin SV and tert.-butylamine (obtained according to the method disclosed in U.S. Pat. No. 3,542,762) or, by using a different reactive derivative of 3-formyl-rifamycin SV obtained according to U.S. Pat. No. 4,174,320 viz. by reacting rifamycin S and a 1,3,5-trisubstituted hexahydro-1,3,5-triazine, possibly in the presence of formaldehyde.

The above mentioned reactive derivative of the amide and thioamide may have various structures and be obtained according to the methods per se known: for example, by reacting an amide or thioamide of formula (II) with an alkyl-fluorosulfonate, the corresponding fluorosulfonate imidate may be obtained; by reacting with a dialkyl sulphate or triethyloxonium fluoroborate and then with sodium alcoholate (or similar alternative methods) an acetal of the compound of formula (II) may be obtained, etc. (See Ahmed M. G. et al., *Chem.Com.*, 1533, 1968; Bredereck H. et al., *Chem.Ber.*, 96, 1350, 1963; Meerwein H. et al., *Liebigs Ann.Chem.*, 641, 1, 1961; Weintraub L. et al., *J.Org.Chem.*, 33, 1679, 1968; GB No. 1,293,590.)

The above described process for making the inventive compounds of formula (I) does however present a drawback deriving from the use of the hydrazone of 3-formyl-rifamycin SV; in fact the latter, despite precautions taken during its preparation, always gives partial cyclization, resulting in diminished yields, non-employment of the most expensive reagent (3-formyl-rifamycin SV) and contamination of the final product. This drawback is already recognized in the U.S. Pat. No. 3,342,810, col.9, lines 5–10.

The derivatives of formula (I) may also be obtained by following a different and superior method, by which a compound of formula

$$NH_2-N=CR_1-NR_2R_3 \qquad (III)$$

is prepared wherein $R_1$, $R_2$ and $R_3$ have the above defined meanings, by reacting hydrazine with a reactive derivative of an amide or thioamide of formula (II) as mentioned above; the said compound of formula (III) is then reacted with 3-formyl-rifamycin SV, or with one of its above-mentioned reactive derivatives, in chloroform, methylene chloride or tetrahydrofuran to give the compound of formula (I).

With this latter method, no cyclization on the 3-formyl-rifamycin SV molecule occurs, the yields are high and the final compound is not contaminated by impurities which are difficult to separate.

The present invention also includes pharmaceutical formulations containing one of the new derivatives of formula (I) having antibiotic acitivity, admixed with one or more solid, liquid or semisolid excipients, which may be administered by oral, parenteral or topical route.

The solid formulations for oral administration include tablets, pills, powders for extemporaneous solution, capsules and granules. In such formulations, one of the active ingredients may also be admixed with an inert support, such as calcium carbonate, starch, lactose, alginic acid, etc. Other inert substances which may be and in practice are included are lubricants, e.g. magnesium stereate.

The liquid formulations for oral administration include solutions, emulsions, suspensions, syrups and elixirs containing, together with the active ingredient, wetting agents, sweeteners, colouring and flavouring agents.

The formulations for parenteral use include sterile solutions, with or without an aqueous solvent, possibly containing wetting agents, emulsifiers and dispersing agents. Sterile powders, lyophilized or not, to solubilize with a suitable liquid agent immediately before use, are also included.

The formulations for topical use include drops, tinctures, lotions, creams, solutions, ointments containing, together with the active ingredient, traditional supports and vehicles.

The percentage of active ingredient in each pharmaceutical formulation varies according to the formulation itself and the therapeutic effect desired in the specific pathologies and correlated posologies.

The instant invention will now be further illustrated by means of the following non-limiting examples.

EXAMPLE 1

Derivative of formula (I) wherein $Y=CH_3-CO$; $R_1=CH_3$; and $R_2=R_3$ are $CH_2CH_3$ 10.6 g (0.066 mole) N,N-diethylacetamide-dimethylacetal is reacted with 3.2 ml (0.066 mole) hydrazine hydrate. An exothermic reaction with formation of a yellow-pink solution occurs.

The so-obtained solution is added at room temperature to 29 g (0.04 mole) 3-formyl-rifamycin SV dissolved in 600 ml tetrahydrofuran. The reaction ends after 15 minutes. The solvent is evaporated under reduced pressure and the residue is crystallized from ethanol.

Yield: 22 g of a crystalline red product, $Rf=0.63$ (TLC, chlorofom:methanol 9:1).

Analysis for $C_{44}H_{60}N_4O_{12}$ (M.W. 836.98): % found C 63.30; H 7.12; N 6.73; O 22.75. % calc. C 63.14; H 7.23; N 6.69; O 22.94.

MS: 836 (M+).

EXAMPLE 2

Derivative of formula (I) wherein $Y=CH_3-CO$; $R_1=R_2=R_3$ are $CH_3$ 1.4 g 3-formyl-rifamycin SV is disssolved in 15 ml THF plus 0.27 ml triethylamine, at room temperature. 0.1 ml $N_2H_4.H_2O$ is added at $0°/+5°$ C. 10 minutes later, 0.5 ml $CH_3C(OCH_3)_2-N(CH_3)_2$ is added at 0° C.

After 5 minutes, the hydrazone is no longer present. The solution is diluted with 50 ml isopropylacetone, washed with dilute acetic acid and then with water and evaporated dry.

The residue is purified by chromatography on silica gel eluting with ethyl acetate-methanol. After concentration to dryness, the residue is crystallized from ethanol.

Yield: 0.5 g (32% of the theoretical).

Analysis: for $C_{42}H_{56}N_4O_{12}$ (M.W. 808.92): % found C 62.50; H 7.01; N 6.95; O 23.80. % calc. C 62.36. H 6.98; N 6.93; O 23.73.

MS: 808 (M+).

EXAMPLE 3

Derivative of formula (I) wherein $Y=CH_3-CO$; $R_1=R_2=R_3$ are $CH_3$ 3.5 g (0.005 mole) Schiff's base obtained from 3-formyl-rifamycin SV and tert.-butylamine is dissolved in 100 ml chloroform and treated with 0.5 ml (0.01 mole) hydrazine hydrate. After 30 minutes reaction, 4 ml (0.02 mole) N,N-dimethylacetamide dimethylacetal is added. After 3 hours reaction, the solvent is evaporated under reduced pressure and the residue is purified by crystallization. Thin layer chromatography on silica gel 60 F 254 Merck, eluent chloroform:methanol 9:1, evidences a single spot, $R_f 0.53$.

Yield: 2.2 g of a crystalline red product, identical in physico-chemical characteristics to that obtained in Example 2.

EXAMPLE 4

Derivative of formula (I) wherein $Y=CH_3-CO$;
$R_1=R_2=R_3$ are $CH_3$ 2.9 ml N,N-dimethylacetamide dimethylacetal is reacted with 0.95 ml hydrazine hydrate.

The yellow solution obtained is dropped into 7.1 g 3-formyl-rifamycin SV dissolved in 500 ml tetrahydrofuran. When the reaction is over, the solvent is evaporated under reduced pressure and the residue is crystallized from ethanol.

Yield: 6.1 g

EXAMPLE 5

Derivative of formula (I) wherein $Y=CH_3-CO$;
$R_1=R_2=R_3$ are $CH_3$ 0.5 ml (0.01 mole) hydrazine hydrate is reacted with 2 ml (0.01 mole) N,N-dimethylacetamide dimethylacetal. The so-obtained solution is dropped, at room temperature, into a solution of 3.5 g (0.005 mole) Schiff's base, obtained from 3-formyl-rifamycin SV and tert.-butylamine, in 100 ml chloroform.

After one hour, the solvent is evaporated under reduced pressure and the residue is crystallized from ethanol.

Yield: 2.8 g

EXAMPLE 6

Derivative of formula (I) wherein $Y=CH_3-CO$;
$R_1=R_2=R_3$ are $CH_3$ 4 ml (0.02 mole) N,N-dimethylacetamide dimethylacetal is treated with 1 ml (0.02 mole) hydrazine hydrate. The solution obtained is dropped, at room temperature, into a solution of 7.2 g (0.01 mole) condensation product between rifamycin S, 1,3,5-tri-tert.butyl-hexahydro-1,3,5-triazine and formaldehyde (obtained according to U.S. Pat. No. 4,174,320), dissolved in 200 ml chloroform. After 6 hours reaction at room temperature, the solvent is evaporated under reduced pressure and the residue is crystallized from ethanol.

Yield: 4.6 g

EXAMPLE 7

Derivative of formula (I) wherein $Y=CH_3-CO$;
$R_1=R_2=R_3$ are $CH_3$ 2 g (0.01 mole) adduct between N,N-dimethylacetamide and methyl fluorosulfonate is dissolved in 5 ml dimethylformamide and treated at room temperature with 0.5 ml (0.01 mole) hydrazine hydrate. The violet solution obtained is dropped into a solution of 1.75 g 3-formyl-rifamycin SV in 50 ml THF containing 1.5 ml triethylamine. After 2 hours reaction, the solution is diluted with water and extracted with chloroform, the organic phase is washed with water, dehydrated and evaporated dry.

The residue is crystallized from ethanol.

Yield: 0.5 g

EXAMPLE 8

Derivative of formula (I) wherein $Y=CH_3-CO$;
$R_1=R_2$ are $CH_3$; $R=CH_2CH_3$ 2 ml (0.01 mole) N-methyl-N-ethyl-acetamide dimethylacetal is reacted with 0.5 ml (0.01 mole) hydrazine hydrate. An exothermic reaction occurs.

The so obtained solution is added to 3.5 g (0.005 mole) 3-formyl-rifamycin SV dissolved in 100 ml tetrahydrofuran. After 15 minutes the reaction is over.

The solvent is evaporated under reduced pressure and the residue is crystallized from ethanol, obtaining the title product in the form of red crystals, $R_f=0.62$ (TLC, chloroform:methanol 9:1).

Yield: 1.1 g

Analysis: for $C_{43}H_{58}N_4O_{12}$ (M.W.822.96): % found C 62.55; H 7.14; N 6.68. % calc. C 62.76; H 7.10; N 6.81.

EXAMPLE 9

Derivative of formula (I) wherein $Y=CH_3-CO$;
$R_1=CH_3$; $R_2=R_3$ are $CH_2CH_2CH_3$ 3.8 g (0.02 mole) N,N-dipropylacetamide dimethylacetal is reacted for about 20 minutes with an equimolecular quantity of hydrazine hydrate and maintained under stirring at a temperature of about 80° C.

The lower phase of the heterogeneous mixture is discarded, the upper phase is added to a solution of 3.5 g (0.005 mole) 3-formyl-rifamycin SV in 100 ml tetrahydrofuran.

After shortly reacting at room temperature, the completeness of the reaction is checked by TLC. After the reaction is completed, the mixture is evaporated dry. The crude product is purified by column chromatography on silica gel, eluting with methylene chloride containing 1-1.5% of methanol. 2 g of the desired product is obtained thereby, $R_f=0.7$ (TLC, chloroform:methanol 9:1)

Analysis: for $C_{46}H_{64}N_4O_{12}$ (M.W. 865.04): % found C 64.12; H 7.36; N 6.55. % calc. 6 63.87; H 7.46; N 6.48.

EXAMPLE 10

Derivative of formula (I) wherein $Y=CH_3-CO$;
$R_1=CH_3$; $R_2=R_3$ are $CH_2-CH=CH_2$ 1 ml hydrazine hydrate is reacted with 4 ml N,N-diallylacetamide dimethylacetal in 20 ml ethyl alcohol. The so obtained solution is added, at room temperature, to 7.2 g 3-formyl-rifamycin SV, dissolved in 150 ml tetrahydrofuran. After 15 minutes the reaction is over. The solvent is evaporated under reduced pressure and the residue is crystallized from ethanol.

Yield: 4.8 g of a red product with $R_f=0.79$ (TLC, chloroform:methanol 9:1).

Analysis: for $C_{46}H_{60}N_4O_{12}$ (M.W. 861.01): % found C 64.03; H 6.96; N 6.50. % calc. C 64.17; H 7.02; N 6.51.

EXAMPLE 11

Derivative of formula (I) wherein $Y=CH_3-CO$;
$R_1=CH_3$; $NR_2R_3$ is piperidine 3.5 g (0.02 mole) N-acetyl-piperidine dimethylacetal is mixed with 1 ml (0.02 mole) hydrazine hydrate. The reaction is exothermic and leads to the formation of a yellow solution which is added, at room temperature, to 7 g (0.01 mole) 3-formyl-rifamycin SV dissolved in 200 ml tetrahydrofuran. After 15 minutes stirring, the reaction mixture is evaporated dry under reduced pressure and the residue is purified by crystallization.

Yield: 1.8 g of a red product, $R_f=0.69$ (TLC, chloroform:methanol 9:1).

Analysis: for $C_{45}H_{60}N_4O_{12}$ (M.W.849.00): % found C 63.80; H 7.15; N 6.58. % calc. C 63.66; H 7.12; N 6.60.

EXAMPLE 12

Derivative of formula (I) wherein $Y=CH_3-CO$; $R_1=CH_3$; $NR_2R_3$ is piperidine 4 ml (0.02 mole) N-acetyl-piperidine dimethylacetal is reacted with 1 ml (0.02 mole) hydrazine hydrate. An exothermic reaction and complete miscibility occur. The so obtained solution is dropped, at room temperature, into a deep blue solution containing 7.2 g of condensation product between rifamycin S, 1,3,5-tri-tert-.butyl-hexahydro-1,3,5-triazine and formaldehyde (obtained according to U.S. Pat. No. 4,174,320) in 200 ml chloroform.

The typical blue colour disappears and a red orange colour is observed. After 15 hours reaction, at room temperature, the solvent is evaporated under pressure and the residue is crystallized from ethanol.

Yield: 5.2 g $R_f=0.69$ (TLC, chloroform:methanol 9:1).

EXAMPLE 13

Derivative of formula (I) wherein $Y=CH_3-CO$; $R_1=CH_3$; $NR_2R_3$ is morpholine 1 ml hydrazine hydrate is reacted with 3.5 ml N-acetylmorpholine dimethylacetal, in absence of solvents. A strong exothermic reaction occurs. On cooling, a solid is formed which is dissolved in tetrahydrofuran. The so obtained solution is added, at room temperature, to 7.2 g 3-formyl-rifamycin SV dissolved in 150 ml tetrahydrofuran. The reaction is over in 30 minutes. The solvent is evaporated under reduced pressure and the residue is crystallized from ethanol.

Yield: 4.1 g of a red crystalline product, $R_f=0.69$ (TLC, chloroform:methanol 9:1).

Analysis: for $C_{44}H_{58}N_4O_{13}$ (M.W.850.97): % found C 61.82; H 6.81; N 6.63. % calc. C 62.10; H 6.87; N 6.58.

EXAMPLE 14

Derivative of formula (I) wherein $Y=CH_3-CO$; $R_1=R_2=R_3$ are $CH_2-CH_3$ 2.7 ml methyl fluorosulfonate is added, at room temperature, to 4.4 g N,N-diethylpropionamide. A solid is formed with heat evolution. The reaction product is disintegrated with ethyl ether and filtered. The so obtained solid is dissolved in 13 ml dimethylformamide and treated with 1.5 ml hydrazine hydrate. The resulting solution is added to 7.2 g 3-formyl-rifamycin SV dissolved in 150 ml tetrahydrofuran containing 4 ml triethylamine. After 1 hour, the reaction is practically complete. The solvent is evaporated under reduced pressure, the residue is dissolved with chloroform, washed with water and the organic phase dried over sodium sulfate. After evaporation to dryness, the residue is crystallized from ethanol.

Yield: 2.3 of a red product, $R_f=0.71$ (TLC, chloroform:methanol 9:1).

Analysis: for $C_{45}H_{62}N_4O_{12}$ (M.W.851.02): % found C 63.19; H 7.32; N 6.55. % calc. C 63.51; H 7.34; N 6.58.

EXAMPLE 15

Derivative of formula (I)-quinone wherein $Y=CH_3-CO$; $R_1=R_2=R_3$ are $CH_3$ 0.6 g product obtained by following Example 4 is dissolved in 50 ml chloroform.

0.5 g manganese dioxide is added and left under stirring for 2 hours, at room temperature.

The suspended matter is filtered off and the solution evaporated dry, obtaining, after crystallization, 0.5 g of the title product in the form of blue-violet crystals, $R_f=0.91$ (TLC, chloroform:methanol 9:1).

EXAMPLE 16

Derivative of formula (I) wherein $Y=H$; $R_1=R_2=R_3$ are $CH_3$ 0.6 g of the product obtained following Example 4 is dissolved in 12 ml of a 5% NaOH solution in ethanol:-$H_2O$ 1:1. The mixture is left under stirring, at room temperature, for 2 hours, then the end of the reaction is controlled by TLC. The product is extracted with chloroform and the solution is washed with water, then the solvent is dried and evaporated. 0.3 g of a red orange product is obtained, $R_f=0.38$ (TLC, chloroform:methanol 9:1).

EXAMPLE 17

Derivative of formula (I)-quinone wherein $Y=H$; $R_1=R_2=R_3$ are $CH_3$ 0.6 g of the desacetylated product obtained according to Example 16 is dissolved in 50 ml chloroform. 0.5 g manganese dioxide is added and left under stirring for 2 hours. The mixture is then controlled by TLC, filtered, and the solvent evaporated dry, thus obtaining the desired product is blue-violet coloured crystals, $R_f=0.67$ (TLC, chloroform:methanol 9:1). Yield: 0.5 g.

Hereunder are furthermore indicated examples illustrative of suitable pharmaceutical compositions containing one of the inventive compounds denoted as active principle:

| Example 18 SYRUP | | |
|---|---|---|
| Active principle | g | 2 |
| Saccharose | g | 50 |
| Agaragar | g | 0.300 |
| Potassium sorbate | g | 0.120 |
| Sodium metadisulfite | g | 0.100 |
| Methyl p-hydroxybenzoate | g | 0.090 |
| Ethyl p-hydroxybenzoate | g | 0.035 |
| Propyl p-hydroxybenzoate | g | 0.025 |
| Saccharine | g | 0.080 |
| Polyoxyethylene-sorbitan monoleate | g | 0.010 |
| Raspberry flavouring | g | 0.500 |
| Purified water up to | ml | 100 |
| Example 19 DROPS | | |
| Active principle | g | 15 |
| Ascorbic acid | g | 0.200 |
| Saccharine | g | 0.500 |
| Diethanolamine | g | 2.600 |
| Sodium metadisulfite | g | 0.100 |
| Disodium salt of ethylenediamine-tetracetic acid | g | 0.010 |
| Ethanol | g | 20 |
| Propylene glycol up to | ml | 100 |
| Example 20 INJECTABLE | | |
| Formulation A - lyophilized | | |
| Active principle | mg | 300 |
| Sodium formaldehyde sulfoxylate | mg | 5 |
| Sodium hydroxide | mg | 10 |
| solvent | | |
| Polyoxyethylene-sorbitanmonoleate | mg | 0.3 |
| Water for injectable compositions up to | ml | 5 |
| Formulation B - lyophilized | | |
| Active principle | mg | 600 |
| Sodium formaldehyde sulfoxylate | mg | 10 |
| Sodium hydroxide | mg | 20 |
| solvent | | |

| -continued | |
|---|---|
| Polyoxyethylene-sorbitan monoleate | mg 0.6 |
| Water for injectable compositions up to | ml 10 |
| Example 21 CAPSULES | |
| Formulation A | |
| Active principle | mg 300 |
| Maize starch | mg 30 |
| Magnesium stearate | mg 10 |
| Hard gel capsule | No. 1 |
| Formulation B | |
| Active principle | mg 150 |
| Maize starch | mg 15 |
| Magnesium stearate | mg 5 |
| Hard gel capsule | No. 1 |
| Example 22 - TABLETS | |
| Formulation A | |
| Active principle | mg 300 |
| Microcrystalline cellulose | mg 100 |
| Lactose | mg 100 |
| Maize starch | mg 30 |
| Talcum | mg 100 |
| Magnesium stearate | mg 5 |
| Gelatine | mg 30 |
| Saccharose | mg 100 |
| Magnesium carbonate | mg 20 |
| Titanium dioxide | mg 10 |
| Erythrosine | mg 3 |
| Formulation B | |
| Active principle | mg 600 |
| Microcrystalline cellulose | mg 100 |
| Lactose | mg 100 |
| Maize starch | mg 50 |
| Talcum | mg 150 |
| Magnesium stearate | mg 10 |
| Gelatine | mg 40 |
| Saccharose | mg 150 |
| Magnesium carbonate | mg 30 |
| Titanium dioxide | mg 15 |
| Erythrosine | mg 5 |

We claim:

1. A rifamycin derivative corresponding to the following formula (I)

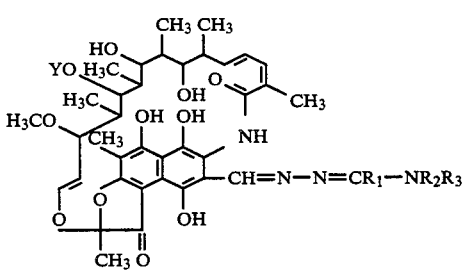

wherein:
Y=H or CH$_3$—CO;
R$_1$ is an alkyl group with up to 4 carbon atoms;
R$_2$ is an alkyl group with up to 6 carbon atoms, an alkenyl group with up to 5 carbon atoms, a cycloalkyl group having from 5 to 7 carbon atoms, phenyl or benzyl;
R$_3$ is an alkyl grouup with up to 6 carbon atoms or an alkenyl group with up to 5 carbon atoms; or
—NR$_2$R$_3$ is pyrrolidinyl piperidinyl, hexahydroazepinyl or morpholinyl.

2. A quinone derivative of a compound of formula (I) according to claim 1.

3. The derivative of claim 1 in which Y is CH$_3$—CO and R$_1$ is methyl.

4. The derivative of claim 3 in which R$_2$ and R$_3$ are methyl, ethyl, propyl, propenyl or together with the nitrogen to which they are attached form a piperidine or morpholine group.

5. The derivative of claim 3 in which R$_2$ is methyl and R$_3$ is ethyl.

6. The derivative of claim 1 in which which R$_1$, R$_2$ and R$_3$ are ethyl and Y is CH$_3$—CO.

7. The derivative of claim 1 in which Y is hydrogen and R$_1$, R$_2$ and R$_3$ are methyl.

8. The quinone derivative of claim 2 in which R$_1$, R$_2$ and R$_3$ are methyl.

9. A process for the preparation of a compound of formula (I) according to claim 1, comprising preparing a compound of formula $$NH_2-N=CR_1-NR_2R_3 \qquad (III)$$

wherein R$_1$, R$_2$ and R$_3$ have the defined meaning, by reacting hydrazine with a reactive derivative of an amide or thioamide of formula

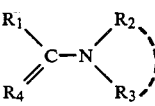     (II)

wherein R$_4$=O or S, and reacting such compound of formula (III) with 3-formyl-rifamycin SV in chloroform, methylene chloride or tetrahydrofuran.

10. A process for the preparation of a compound of formula (I) according to claim 1, comprising dissolving the hydrazone of the 3-formyl-rifamycin SV in a solvent and reacting said hydrazone with a reactive derivative of an amide or thioamide of formula

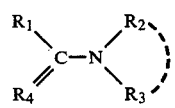     (II)

wherein R$_1$, R$_2$, R$_3$ and

are as defined in claim 1 and R$_4$=O or S.

11. A process according to claim 9 or 10, comprising obtaining the said reactive derivative of the compound of formula (II) by reacting the compound of formula (II) either (a) with an alkyl-fluorosulfonate to give the corresponding adduct, or (b) with a dialkyl-sulfate or with a triethyloxonium-fluoroborate, and then with sodium alcoholate, to give the corresponding acetal.

12. A process for the preparation of a compound of formula (I) according to claim 1, comprising reacting a compound of formula $$NH_2-N=CR_1-NR_2R_3 \qquad (III)$$

wherein R$_1$, R$_2$ and R$_3$ are as above defined in claim 1, with a Schiff's base of 3-formyl-rifamycin SV with an alkyl amine.

13. A process for the preparation of a compound of formula (I) according to claim 1, comprising reacting a compound of formula NH$_2$—N=CR$_1$—NR$_2$R$_3$ (III) wherein R$_1$, R$_2$, R$_3$ are as defined in claim 1, with a reactive derivative of 3-formyl-rifamycin SV obtained by reacting rifamycin S and a 1,3,5-tri-substituted hexahydro-1,3,5-triazine.

14. A process according to claim 13, comprising obtaining such reactive derivative of 3-formyl-rifamycin SV in the presence of formaldehyde.

15. A pharmaceutical composition having antibacterial and antiviral activity containing as the active substance an effective antibacterial and antiviral amount of a compound of formula (I) of claim 1 and a pharmaceutically acceptable carrier.

16. The pharmaceutical composition of claim 15 in which Y is $CH_3—CO$ and $R_1$ is methyl.

17. The pharmaceutical composition of claim 16 in which $R_2$ and $R_3$ are methyl, ethyl, propyl, propenyl or together with the nitrogen to which they are attached form a piperidine or morpholine group.

18. The pharmaceutical composition of claim 16 in which $R_2$ is methyl and $R_3$ is ethyl.

19. The pharmaceutical composition of claim 15 in which $R_1$, $R_2$ and $R_3$ are ethyl.

20. The pharmaceutical composition of claim 15 in which Y is hydrogen and in which $R_1$, $R_2$ and $R_3$ are methyl.

* * * * *